(12) United States Patent
Stenfeldt et al.

(10) Patent No.: US 11,878,142 B2
(45) Date of Patent: Jan. 23, 2024

(54) INFUSION SYSTEM FOR SHORT-LIVED RADIOPHARMACEUTICALS

(71) Applicant: MedTrace Pharma A/S, Kongens Lyngby (DK)

(72) Inventors: Martin Stenfeldt, Vedbæk (DK); Rune Kristensen Wiik, Hinnerup (DK); Peter Larsen, Værløse (DK)

(73) Assignee: MedTrace Pharma A/S, Kongens Lyngby (DK)

( * ) Notice: Subject to any disclaimer, the term of this patent is extended or adjusted under 35 U.S.C. 154(b) by 1221 days.

(21) Appl. No.: 16/472,091

(22) PCT Filed: Dec. 21, 2017

(86) PCT No.: PCT/EP2017/084102
§ 371 (c)(1),
(2) Date: Jun. 20, 2019

(87) PCT Pub. No.: WO2018/115286
PCT Pub. Date: Jun. 28, 2018

(65) Prior Publication Data
US 2020/0086036 A1    Mar. 19, 2020

(30) Foreign Application Priority Data
Dec. 21, 2016 (EP) .................... 16205836

(51) Int. Cl.
*A61M 5/00* (2006.01)
*A61M 5/142* (2006.01)
(Continued)

(52) U.S. Cl.
CPC ........ *A61M 5/007* (2013.01); *A61M 5/14212* (2013.01); *A61M 5/16813* (2013.01);
(Continued)

(58) Field of Classification Search
CPC .............. A61M 5/007; A61M 5/14212; A61M 5/16813; A61M 5/16827; A61M 39/223; A61M 2005/1403
See application file for complete search history.

(56) References Cited

U.S. PATENT DOCUMENTS 4,562,829 A    1/1986 Bergner
2005/0085682 A1    4/2005 Sasaki

FOREIGN PATENT DOCUMENTS

EP    1616587    1/2006
EP    2179758    4/2010
(Continued)

OTHER PUBLICATIONS

International Search Report and Written Opinion for International Application No. PCT/EP2017/084102 dated Apr. 11, 2018 (12 pages).
(Continued)

*Primary Examiner* — Nathan R Price
*Assistant Examiner* — Tania Ismail
(74) *Attorney, Agent, or Firm* — Quarles & Brady LLP (57) ABSTRACT

A non-surgical method of delivering a liquid radioactive solution from a source to a recipient comprising the steps of: determining a desired recipient level of radioactivity and recipient volume of the radioactive solution to be delivered
(Continued)

to the recipient, providing a first valve having a waste position and a recipient position, providing a bolus conduit, a waste conduit and a recipient conduit, each conduit having a valve end being connected to said first valve, so that the first valve can establish a waste flow path in the waste position and a recipient flow path in the recipient position, the recipient flow path being different from said waste flow path, the bolus conduit comprising a measuring section and an internal volume, the internal volume being approximately equal to the desired recipient volume of the radioactive solution to be delivered to the recipient, arranging said first valve in the waste position, transporting a first amount of said radioactive solution through said waste flow path, the first amount of said radioactive solution having an initial level of radioactivity that is at least approximately equal to or higher than the desired recipient level of radioactivity and an initial volume that is larger than the internal volume of said bolus conduit, providing a radiation detector, the radiation detector being operable to measure a level of radioactivity of the radioactive solution in said measuring section, measuring a reference level of radioactivity of said radioactive solution present in said measuring section, wherein when the reference level of radioactivity is approximately equal to an injection level of radioactivity, the method further comprises the steps of: arranging the first valve in the recipient position, and transporting the radioactive solution present in the bolus conduit through the recipient flow path.

13 Claims, 4 Drawing Sheets (51) Int. Cl.
    *A61M 5/168*     (2006.01)
    *A61M 5/36*     (2006.01)
    *A61M 5/14*     (2006.01)
    *A61M 39/22*     (2006.01)

(52) U.S. Cl.
    CPC ........ *A61M 5/16827* (2013.01); *A61M 5/365* (2013.01); *A61M 39/223* (2013.01); *A61M 2005/1403* (2013.01); *A61M 2205/15* (2013.01); *A61M 2205/18* (2013.01)

(56) References Cited

FOREIGN PATENT DOCUMENTS

JP     2006-017660     1/2006
WO     1996/014099     5/1996

OTHER PUBLICATIONS

Stöcklin, G. And Pike, V.W. (1997) Radiopharmaceuticals for Positron Emission Tomography—Methodological Aspects. Kluwer Academic Publishers [English translation of relevant parts].

INFUSION SYSTEM FOR SHORT-LIVED RADIOPHARMACEUTICALS

CROSS REFERENCE TO RELATED APPLICATION

The present application is a U.S. national stage of International Application PCT/EP2017/084102, filed Dec. 21, 2017, which claims the benefit of priority to European Patent Application No. 16205836.6, filed Dec. 21, 2016, the contents of each are incorporated herein by reference in their entireties.

FIELD OF THE INVENTION

The present invention relates in a first aspect to a non-surgical method of delivering a liquid radioactive solution from a source to a recipient, in a second aspect to an infusion system for delivering a liquid radioactive solution from a source to a patient and in a third aspect to a non-surgical method of dosing a liquid radioactive solution.

BACKGROUND OF THE INVENTION

Radioisotopes (also called radionuclides) have several applications in medical therapy, imaging and research. Through the emission of positrons, beta minus particles, high energy gamma electrons or auger electrons in close proximity to a cell nucleus, different imaging/measurement techniques permit imaging and measuring of physiological processes within the human body. Radio isotopes can further be used as therapeutics to illicit cell death within the field of oncology if injected intravenously.

Radioisotopes such as $^{18}$F, $^{11}$C, $^{15}$O, $^{14}$O, $^{82}$Rb and $^{13}$N are typically used in labelling radiopharmaceuticals for use in PET. Today, dosing of non-radioactive pharmaceuticals for intra venous (I.V.) injection in hospital or clinical environments are typically done volumetric from a standard solution of known pharmacological dose strength. In other uses the dosing is done by drawing up a specific volume of a non-radioactive pharmaceutical from a known dose strength, and mixing within syringe the drawn up dose with a non-cross acting solution for dispensing i.e. physiological saline or water for injection. This methodology however cannot be used within the field of radiopharmaceuticals, since the half-life associated with these radioisotopes is very short, typically on the order of minutes (except $^{18}$F which has a half-life of almost two hours). Oxygen-15 ($^{15}$O) has a half-life of 122.24 seconds and is one of the most suitable radioactive isotopes for use in PET for quantifying regional cerebral blood flow (rCBF), and for quantifying regional myocardial blood flow (rMBF).

Most systems for producing radioactive water in compliance with the requirements for manufacturing radiopharmaceuticals for human use under transferred into a certified laboratory environment-typically to a synthesis device housed in a HotCell, wherein the radioactive gas mixture is converted from $^{15}$O—$O_2$ into $H_2{}^{15}$O using either a catalytic process or heating to approximately 800° C. in connection with infusion of $H_2$. The converted $H_2{}^{15}$O is then typically bubbled into a saline solution in a reservoir, thus trapping the $H_2{}^{15}$O in said solution. This $H_2{}^{15}$O-solution is often referred to as the source solution.

The source solution is then manually transferred from the reservoir into a draw up room or similar, and the desired dose for the patient is then typically manually drawn up into a syringe, which is then manually transported into a PET-scanning room.

Due to the radioactive nature of radiopharmaceuticals, the effective concentration within the source solution will always be decreasing exponentially at a rate proportional to the decay constant of the radioactive isotope (or isotopes) intrinsic in the pharmaceutical.

For this reason, the way radiopharmaceuticals are dosed today is by measuring the radioactivity in Becquerel or Curie, and timing the point of injection with the desired dose to the patient. Typically, under the manual regime the double amount of desired radioactivity or more is measured in a dose calibrator and extracted. A timer is started, and when the radioactivity has decreased due to the decay of the relevant radioisotope and reached the desired level, the extracted amount is transferred to the patient. Because of the short half-life of the radioisotopes the timing of the extraction and injection has to be very precise to determine the actual amount of radioactivity transferred to the patient.

Due to the short half-life of $^{15}$O, this manual way of extracting a dose is not possible in a manner which allows for a consistent dose volume at the same time as the radioactivity level of the desired dose is known. It is only possible to use $^{15}$O under the current rules for GMP manufacturing or the practise of pharmacy in the aforementioned manner, wherein for the individual patient dosing the radioactive level is kept consistent but it will not be possible to have a consistent volume for multiple doses to the same patient, or in a similar manner where the volume of dosing between patients receiving the same radioactive dose will be consistent. Due to these constraints, and the fact that $^{15}$O $H_2O$ is mainly used as a perfusion agent, it's current practical clinical use is limited in extent to research purposes since a broad clinical usage will require consistency in volumetric dosing and knowledge of the dose volume as well as the injection speed in order to assess the flow of O-15 H2O within the body via PET scanning apparatus and software algorithmic means.

The manual handling of the radioisotopes from the certified lab and into the scanner suite where the patient is waiting is safe with regards to the patient, but due to the repeated radioactivity exposure to the medical personal, it is not feasible for routine patient examinations, since the medical personal is subjected to unwanted and dangerous radiation with every extraction and injection performed.

Furthermore, the manual handling allows the dispensing of well-determined volumes of radioisotopes, but cannot provide accurate volumes having a defined accurate radioactivity at a particular time point.

A solution to the problem is to take a homogenously distributed stem solution containing a radiopharmaceutical, and dosing this radiopharmaceutical into a known fixed volume while waiting for the radioactivity to decay until the desired dose for the individual patient.

Such a methodology is currently impractical in clinical settings due to the exponential decay of the stem solution. Initially the effective concentration (Becquerel/ml) is high or very high, and at a later point the effective concentration will be low or very low. In order to dose with a fixed volume in the aforementioned method, a cutoff level will exist at which point the prescribed dose volume will no longer be able to contain the prescribed radioactive dose, and the remaining dose within the stem solution would have to be discarded. The methodology is impractical in the sense that discarding radiopharmaceuticals due to a desire to keep a fixed volume is highly costly, while at the same time the nature of most clinically used radiopharmaceuticals today is to either bind selectively to targets in vivo, or participate in metabolic processes, or act as non-interacting perfusion agents.

However, a selection of radiopharmaceuticals exists, where the intrinsic purpose of the radiopharmaceutical is to act as a flow marker, and unspecific binding or metabolism of the radiopharmaceutical is highly undesired. For this class of radiopharmaceuticals in particular, a means of dosing effectively in terms of both radioactive dose as well as volume and injection speed is highly desired, as this would allow for the creation of very homogenous injection profiles, and by varying the injection speed both between injections and during injections the injection profile may be modified further to suit different clinical applications.

Thus, there is a need for an infusion system that is capable of dosing, and/or in some embodiments injecting, specified amounts of a radioactive solution (such as $H_2{}^{15}O$) with high precision (thus being well-determined in terms of volume and radioactivity at a given time point) and with a negligible risk for both patients and medical personnel.

SUMMARY OF THE INVENTION

An object of the invention and/or of the present disclosure may be seen as to provide an infusion system for delivering a radioactive solution, a method of dosing and a method of delivering a radioactive solution which avoids, solves or lessens one or more of the above-mentioned drawbacks.

According to the invention, these and further objects may be met by a non-surgical method of delivering a liquid radioactive solution from a source to a recipient comprising the steps of:

determining a desired recipient level of radioactivity and recipient volume of the radioactive solution to be delivered to the recipient, providing a first valve having a waste position and a recipient position, providing a bolus conduit, a waste conduit and a recipient conduit, each conduit having a valve end being connected to said first valve, so that the first valve can establish a waste flow path in the waste position and a recipient flow path in the recipient position, the recipient flow path being different from said waste flow path, the bolus conduit comprising a measuring section and an internal volume, the internal volume being approximately equal to the desired recipient volume of the radioactive solution to be delivered to the recipient, arranging said first valve in the waste position, transporting a first amount of said radioactive solution through said waste flow path, the first amount of said radioactive solution having an initial level of radioactivity that is at least approximately equal to or higher than the desired recipient level of radioactivity and an initial volume that is larger than the internal volume of said bolus conduit, providing a radiation detector, the radiation detector being operable to measure a level of radioactivity of the radioactive solution in said measuring section, measuring a reference level of radioactivity of said radioactive solution present in said measuring section, wherein when the reference level of radioactivity is approximately equal to an injection level of radioactivity, the method further comprises the steps of:

arranging the first valve in the recipient position, and transporting the radioactive solution present in the bolus conduit through the recipient flow path.

Since the radioactive concentration will change with time due to decrease in the nuclide radioactivity it is always necessary to provide a reference time. As with all statements involving radioactivity, it is necessary to include a reference date and time of standardization. For radionuclides with a half-life period of less than 21 minutes, a more precise statement of the reference time is required including time of day in addition to date.

Thus one of the great strength point of the method lies in the ability to dispense a known volume properly whilst also knowing the radioactivity. Especially for flow tracers, it is important to know the injection profile which is based on volume and the injection rate. But due to regulatory accounts i.e. the radioactive dose, it has up until know been necessary to sacrifice the accuracy of the volume in regard to knowing the injected radioactive dose.

The general regulatory requirements in relation to IV injections requires that the injection volume during practice of medicine and practice of pharmacy is known. As well as the strength i.e. the radioactivity of the dose described in activity/ml or mg/ml for non-radioactive drugs. Clinical significance is secondary but important as the standard radioactive solution volumes allows for precise and comparable data bases for blood flow in many patients. Further the method and system according to the invention increases the reproducibility of the individual patient.

In term of the present disclosure, the term "recipient" is to be understood as a destination for the radioactive solution. The radioactive solution may from this destination be transferred elsewhere depending on the system and the surroundings.

The recipient may in some embodiments be the end of the recipient/dosing flow path.

The recipient may in some embodiments be a device at the end of the dosing flow path/recipient flow path, such as a receptacle or an IV bag.

The recipient may in some embodiments be a patient or a catheter in direct fluid connection with a patient.

The bolus may in an embodiment be transferred from the recipient to a patient.

Thus the skilled person will understand, that the recipient may be a variation of different devices or patients depending on the system setup.

In terms of the present disclosure, the term "bolus" may be defined as; a specific amount of the radioactive solution, the amount having a well-defined volume and radioactivity level.

In an embodiment said bolus has a substantially cylindrical body and a homogeneous radioactivity distribution throughout the volume of the bolus.

In another embodiment said bolus has a substantially cylindrical body and a homogeneously distributed radioactivity content throughout the volume of the bolus.

In another embodiment said bolus has a substantially cylindrical body and a constant radioactivity profile measured along the longitudinal axis of said substantially cylindrical body.

In an embodiment said bolus has a substantially cylindrical body and an indistinguishable radioactivity concentration at any point within the volume and/or boundaries of the bolus.

In an embodiment said bolus has a substantially cylindrical body and a negligible difference in radioactivity concentration between any two points within the volume and/or boundaries of the bolus.

If and/or when the administered dose (D) dose of a radiopharmaceutical having a radioactive half-life of <21 minutes is administered to a patient, said dose should be of a size suitable to the detection limit of the scanner, local scanner settings and conditions as well as the individual patients age, weight, sex and ethnicity. It is foreseen that the size of (D) shall likely decrease from current levels with the advent of improved detection capabilities of PET-scanners, and also drop by changes in legislation to fulfill the "As Low As Reasonably Achievable" (ALARA) principle, but (D) shall never decrease to or beyond a point by which the principal fulfilment of the diagnostic reasons for administering the dose become impossible. (D) is likely to be within the range of 5 MBq up to 5.000 MBq, but currently (D) will be preferably within the 250-500 MBq range, and in the near future preferably within the 100-250 MBq range. In the distant future (D) will be preferably be within 10-100 MBq. Most preferably (D) is 400 MBq plus or minus a range of up to 10% permissible as std. variations of radioactive activity dose administrations within the practice of medicine.

Likewise, the bolus volume (V) should be of a size to allow for a rapid introduction into the body, and suitable as regards the individual patients age, weight, sex and ethnicity. For different diagnostic purposes (V) will be within the range of 0.05-50 ml. Preferably (V) will be within the range of 1-5 ml, and most preferably (V) is 2 ml plus or minus a range of up to 10% permissible as std. variations for pharmaceutical volume administrations within the practice of medicine. It is foreseen that the size of (V) may decrease from current levels with the advent of improved administration lines or pump functionalities.

The injection speed (S) should be sufficiently fast to allow for rapid introduction of the volume (V) into the body, and suitable as regards the individual patients age, weight, sex and ethnicity. (S) will be within the range of 0.1 ml/s-5 ml/s, and preferably within the range of 1 ml/s-3 ml/s. (S) is most preferably 2 ml/s. It is likely that (S) may increase with the advent of improved PET scanner data acquisition from radiation detectors. However, lower injection speeds may also become relevant for certain applications of the present invention.

In addition, the term "radioactive concentration" is generally applied to solutions of a radioactive solution. The radioactive concentration of a solution refers to the amount of radioactivity per unit volume of the solution. An example of units for radioactive concentration would be mega Becquerel per millilitre (MBq/ml). Since the radioactive concentration will change with time due to decrease in the nuclide radioactivity it is always necessary to provide a reference time. For short lived radionuclides the reference time will be more precise including time of day in addition to date.

It is well known to people skilled in the art, that it is uppermost essential to know the accurate properties of the bolus before injection and that the injection and bolus is reproducible, not only in the same patient but also across an entire group of patients or patient cohort. This is enabled with the invention according to the first, second and third aspects.

The clinical significance of this is that with a 2 ml injected volume to cardiac ischemia, it is possible to catch the entire injected bolus of the radioactive solution (or a significant part thereof) in the right side of the heart during one heartbeat, and learn much more about the right heart side than know today.

Thereafter the radioactive solution will pass the lungs where a substantial mixing of the solution in a larger volume will occur.

Further, the solution in the larger volume will return to the heart where it feeds the heart muscle through the coronary artery and the three sub arteries.

It is the relative flow between the heart at rest and the heart of the load that is important. Therefore, bolus reproducibility in both studies are very significant for the comparison.

There exist currently no feasible imaging techniques to examine the right side of the heart, neither with respect to the stroke volume/functionality or to the heart's own blood supply to its right side.

Thus the possibility to deliver a narrow well-defined bolus will make a remarkable difference compared to the current infusion systems and delivery methods.

Also in prior art infusion systems some of the isotopes have a relative long half-life such as FDG compared to O-15 water, and a considerably longer production time (about 4 hours for FDG at about 5 min for O-15 water), which means that FDG has an actual shelf life, where excess produced FDG can be store, which cannot be with O-15 water because it is practically worthless shortly after it is produced.

To obtain the liquid radioactive solution, that may be transported to the recipient, prior art systems have to apply a partially manual mixing/dilution of the highly radioactive isotopes (such as 18 F-labeled FDG) with a dilution liquid such as saline water in a plurality of different containers. The infusion system and method of delivering a liquid radioactive solution according to the invention is much more simplified and easy in that overfills a loop, thus avoiding the need to add more diluting liquid or radioactive isotopes after the loop has been filled.

It is to be understood that the liquid radioactive solution, is a homogeneous radioactive solution comprising a radio-pharmaceutical and a solution media, where the combination constitutes an injectable media as per current pharmaceutical standards.

In the scope of the present invention, the term "the internal volume being approximately equal to the desired recipient volume of the radioactive solution to be delivered to the recipient" is to be interpreted as the internal volume differs at most ±5%, preferably at most 2%, more preferred at most 1% from the desired recipient volume of the radioactive solution.

In an embodiment the internal volume differs at most ±5%, preferably at most 2%, more preferred at most 1% from the desired recipient volume of the radioactive solution.

When determining the desired recipient level of radioactivity, the level may take into account a possible change in the radioactivity from the measurement of the injection level of radioactivity to the actual entry into the recipient of the radioactive solution.

A person skilled in the art will understand, that a valve having two different positions (such as a waste position and a recipient/dosing position) does not limit the valve to having only these positions.

In terms of the present disclosure the term "valve" also comprises a valve having a plurality of inlets and outlets.

In an embodiment the first valve is a three ways valve.

In terms of the present disclosure, when referring to a level of radioactivity, such as in the wording "the first amount of said radioactive solution having an initial level of radioactivity", this level of radioactivity is to be understood as the amount of ionizing radiation released by the radioactive isotopes within the homogeneous solution at a given point in time. The unit of measure for radioactivity is Becquerel (Bq). Due to the decay of the isotopes, this level of radioactivity decreases with time.

In an embodiment the methods according to the first and third aspects or the infusion system according to the second aspect relates to the use of the radioactive solution in blood flow imaging using PET (Positron emission tomography) scanning technology or SPECT (photon emission computed tomography) scanning methodology.

Dose calculation of the amount of activity that reaches the recipient (when the recipient is a human patient) is weighted in relation to the target organ, the resultant activity from nearby organs that radiate in the direction of the target organ.

One of the advantages in using radioactive O-15 is that it will not (a negligible amount) deposit in the organs and the relation with the narrow bolus (know volume and activity, quick injection) will render the clearance obsolete.

In an embodiment the bolus conduit comprises a source inlet adapted to receive the radiopharmaceutical solution from the source, the waste conduit comprises a waste outlet adapted for flow out of said waste conduit and the recipient/dosing conduit comprises a recipient/dosing outlet adapted for flow out of said recipient/dosing conduit.

As used herein, the expression "the injection level of radioactivity of the radioactive solution differs at most ±10% from the desired recipient level of radioactivity" means that, at the point in time where the solution is injected, the specific activity of the solution (as measured in e.g. Bq) shall differ at most ±10% from the predetermined desired recipient level decided by the operator. If, for example, the desired recipient level of the solution is 200 Bq, then the actually delivered solution by the infusion system of the invention will have a specific activity in the range of 180-220 Bq.

The infusion system according to the present invention can however operate with more narrow limits than ±10% as regards both level of radioactivity and solution volume. Ranges of ±7%, ±5%, ±2% and even ±1% are possible in most cases.

In the present invention the injection level of radioactivity is to be understood as the level of radioactivity measured a given point in time, where the injection (transportation of the solution present in the bolus conduit to the recipient) is initiated. In the present invention the reference level of radioactivity is to be understood as the level of radioactivity of liquid present in the bolus conduit. The reference level is preferably measured continuously.

In an embodiment the injection level of radioactivity of the radioactive solution differs at most ±10%, preferably at most ±7%, more preferred at most ±5% from the desired recipient/final level of radioactivity.

In an embodiment the injection level of radioactivity of the radioactive solution is approximately equal to the desired recipient/final level of radioactivity.

In an embodiment the internal volume of said bolus conduit differs at most ±10%, preferably at most ±7%, more preferred at most ±5% from the desired recipient/final volume of the radioactive solution.

Thereby the radioactive solution that is delivered to the recipient has a well-known volume, activity level and transportation speed, which renders it possible to determine and visualise an injection profile of the solution to the recipient.

This is the case both when the recipient is a means, from where the radioactive solution may subsequently be transferred to a patient, or when the recipient is a patient and the radioactive solution is transferred directly to the patient.

In an embodiment the first valve has a third position, the third position of the first valve closing the valve end of the bolus conduit, so that the radioactive solution in the bolus conduit cannot flow through the first valve.

In terms of the present disclosure, the term "Intravenous bolus injection" may be defined as; an administration of a bolus through the intravenous route over a negligible period of time.

In an embodiment the method of delivering/dosing a liquid radioactive solution, further comprising the steps of:
providing a second valve having an inlet position and a flushing position,
providing a flushing conduit and a source conduit, each conduit having a valve end being connected to said second valve, the source conduit being adapted for transporting the first amount of said radioactive solution from the source into the bolus conduit, when the second valve is in the inlet position,
providing a flushing liquid reservoir comprising a flushing liquid, said flushing liquid reservoir being connected to said flushing conduit,
providing a flushing device being adapted for transporting the flushing liquid from the flushing liquid reservoir through said flushing conduit and into the bolus conduit, when the second valve is in the flushing position.

In an embodiment the first amount of said radioactive solution has a volume that is 1-2 times larger than the internal volume of the bolus conduit.

Thereby it is ensured that the bolus conduit is completely filled with only the radioactive solution in a homogeneous manner, and any residue of flushing solution is removed from the bolus conduit.

It is to be understood that the bolus conduit is overfilled with the homogeneous radioactive solution so that the relevant radiopharmaceutical still has a relevant level of radioactivity left, when the bolus conduit is completely filled. This is also applicable for isotopes with half-lives led than 3 minutes.

In an embodiment the flushing device is a computer controlled syringe.

In an embodiment the second valve is a three-way valve.

It is to be understood that the first and the second valve may be the same valve having a plurality of inlets and outlets.

In an embodiment, before the step of transporting a first amount of said radioactive solution through said waste flow path, the second valve is arranged in the flushing position, and the flushing liquid is transported through the flushing conduit and through the bolus conduit.

In an embodiment the first valve is positioned in the waste position, so that the flushing liquid is transported through the waste flow path.

The flushing liquid may flow through the waste flow path, so that the flushing liquid exits the infusion system through the waste outlet.

Thus any residue present in the bolus conduit will be flushed out of the system, so that when the first amount of radioactive solution is transported into the bolus conduit, no cross contamination will occur and a homogeneous solution will be obtained.

In an embodiment the first valve is positioned in the recipient/dosing position, so that the flushing liquid may be transported through the recipient/dosing flow path.

Thereby it is possible to transport flushing liquid (such as saline water) directly to the end of the recipient/dosing flow path and/or to the recipient. In some embodiments, the recipient may be a biological tube (i.e. artery or vein). Here it is in some situations desirable to continuously transport a small amount of saline water in to the tube up until the initiation of the transport of the first amount of radioactive solution, to ensure that the biological tube is open and does not collapse.

In an embodiment the step of transporting the radioactive solution present in the bolus conduit through the recipient/dosing flow path comprises:
arranging the second valve in the flushing position, and transporting the flushing liquid through the flushing conduit, through the bolus conduit and the recipient/dosing conduit, whereby the liquid radioactive solution in the bolus conduit is moved through the recipient/dosing flow path and to the recipient.

Thereby the flushing liquid pushes the radioactive solution in front of itself all the way to the recipient or the end of the recipient/dosing flow path.

The bolus of the radioactive solution will experience a minor amount of dilution with the flushing liquid at each end, but since this is reproducible in every transportation of the bolus and is limited, it will not influence the bolus effect when reaching the recipient.

In an embodiment the specific internal volume of the bolus conduit is approximately 0.1-50 ml, preferably approximately 1-10 ml and most preferred approximately 2 ml.

In an embodiment the entire infusion system is exchangeable.

Additionally, or alternatively, the bolus conduit is exchangeable.

Thereby a specific infusion system and/or bolus conduit with a specific internal volume may be selected for different patients and/or different measurement requirements.

Thus providing an easy and cost effective way of switching between different measurements with different requirement, whilst still ensuring no cross contamination between patients.

In an embodiment an injection speed of the radioactive solution to the recipient is approximately 0.05-7 ml/second, preferably approximately 1-5 ml/second and most preferred approximately 2 ml/second.

In the term of the present disclosure the term "transportation speed" is used interchangeable with the term "injection speed". Both terms are to be understood as the velocity at which a liquid is transported.

It is important that the radioactive solution delivered to the recipient has a narrow volume and is delivered quickly. By narrow is meant that the solution amount is well defined and accurate, whilst also having a reproducible volume.

Hereby the system is sufficiently fast and efficient to be capable of transporting radioactive solutions with high radioactivity concentration such that the volume of the injected bolus can be kept low.

This ensures standardizes procedures which may be compared between different recipients.

E.g. in the use of the radioactive solution in blood flow imaging for cardiac measurements using PET (Positron emission tomography) scanning technology or SPECT (photon emission computed tomography) scanning methodology, the optimal recipient volume of the radioactive solution is approximately 2 ml and an optimal transportation speed is approximately 2 ml/second.

In this example with the 2 ml volume and 2 ml/second speed, the radioactive volume in the bolus conduit is emptied in approximately 1 second.

In an embodiment, in the step of transporting the flushing liquid through the flushing conduit and through the bolus conduit, the liquid radioactive solution in the bolus conduit is moved out of said bolus conduit in less than approximately 5 seconds, preferably less than 2.5 seconds, and more preferred approximately 1 second.

In an embodiment, in the step of transporting the liquid radioactive solution in the bolus conduit through the recipient conduit to the recipient, the liquid radioactive solution is transported out of said recipient conduit and to said recipient in less than approximately 10 seconds, preferably less than 5 seconds, and more preferred approximately less than 3 second.

Traditional prior art systems will require up to around 2 minutes or more to transport a radioactive solution (such as O-15) water from a source (such as a hot-cell) to a recipient (such as a patient).

The infusion system and method of delivering a liquid radioactive solution (such as O-15 water) is able to transport the radioactive solution from the source to the recipient in 20 seconds or less, using a preferred transportation speed of 2 ml/second with a maximum volume of up to 20 ml.

From initiation of the transport of the first amount of radioactive solution through the waste flow path (with a 2 ml bolus conduit), the selected radioactive solution is ready for transport to the patient in less than approximately 10 seconds.

In an embodiment the measuring section is spiral-shaped or helically shaped or coil shaped or looped shaped.

In an embodiment the measuring section comprises at least 15 windings.

In an embodiment the radiation detector is arranged so that said measuring section wreathes said part of the radiation detector, the radiation detector being operable to determine a level of radioactivity of the solution in the measuring section.

The principle in the loop construction is that the radioactive volume is placed symmetrically along the centerline of the radioactivity sensor and relatively close to it. This is to ensure that any variation in the placement of the loop, which is exchanged daily, will have minimal influence on the measurements of the radioactivity sensor. Variations in placement could be caused e.g. by production variation in the geometry of the inside of the loop part. The principle of the loop construction ensures that a misplacement will both cause some part of the radioactive volume to be slightly closer to the sensor and some part to be equally further away, giving only a small variation in what is actually sensed by the sensor.

In an exemplary embodiment wherein the bolus conduit comprises a 2 ml volume of radioactive solution, the loop configuration will be able to obtain the same principle effect on the stability of the sensor's measurements even though changes should occur in the variables of its construction which are number of windings, length of coil, inner diameter of tube and to some extent the distance with which it is placed around the radioactivity sensor.

In another embodiment the bolus conduit comprises 5 ml. Here the same variables will define the exact shape of the given loop and will not be of great influence on the principle of the loop construction.

Furthermore, the loop principle may be formed by another construction that by any suitable means ensures, that the radioactive volume is placed symmetrically around the radioactivity sensor along its center axis and relatively close to it.

In an embodiment the first valve and the second valve are arranged adjacent to the coil shaped measuring section.

In an embodiment the length of the bolus conduit is approximately equal to the length of the measuring section.

In an embodiment a sterile filter is arranged between the source and the bolus conduit, so that the radioactive solution from the source flows trough said sterile filter before reaching the bolus conduit.

The sterile filter may be a vented filter. This ensures that any remaining air in the solution may be expelled before entering the infusion system.

This is an additional safety feature ensuring safety of the recipient and a homogeneous radioactive solution.

In an embodiment the source may be a radioactive source in liquid form capable of fulfilling the criteria for an injectable radiopharmaceutical. Said source may be connected with a radioactive generator or a cyclotron or any radioactive starting substance.

It is to be understood that the invention is adaptable apply all currently known radioactive sources in liquid form, whereby the invention unhindered retains its purpose of accuracy in dosing.

In an embodiment the radioactive solution comprises a radiopharmaceutical having a radioactive half-life of less than 21 minutes, preferably less than 10 minutes, more preferred less 3 minutes.

In an embodiment the isotopes of the radiopharmaceutical are selected from a group comprising radioisotopes capable of undergoing beta plus decay such as; O-14, O-15, N-13, Rb-82.

In another embodiment, the isotopes of the radiopharmaceutical are selected from a group comprising isotopes capable of undergoing beta minus decay such as; O-19, O-20 with a half-life below 21 minutes, whereby the radioactive nature of the beta minus decay gives rise to imaging properties of the isotope either directly from the radioactive decay or through scattering.

A person skilled in the art would recognize that the invention described herein could be used independent of the imaging properties of the isotope to dose therapeutic radiopharmaceuticals, where the therapeutic element is related to the beta minus decay of the isotope.

In an embodiment the infusion system and/or the method of delivering a radioactive solution comprises a therapeutic radiopharmaceutical.

In yet another embodiment the isotopes of the radiopharmaceutical are selected from a group comprising isotopes capable of undergoing alpha decay with a half-life below 21 minutes, whereby the radioactive nature of the alpha decay gives rise to imaging properties of the isotope either directly from the radioactive decay or through scattering.

A person skilled in the art would recognize that the invention described herein could be used independent of the imaging properties of the isotope to dose therapeutic radiopharmaceuticals where the therapeutic element is related to the alpha decay of the isotope.

In another embodiment the isotopes of the radiopharmaceutical are selected from a group comprising Auger electron emitting isotopes with a half-life of below 21 minutes, whereby the radioactive nature of the auger electron emission gives rise to imaging properties of the isotope either directly from the radioactive decay or through scattering.

A person skilled in the art would recognize that the invention described herein could be used in-dependent of the imaging properties of the isotope to dose therapeutic radiopharmaceuticals where the therapeutic element is related to the auger electron emission property of the isotope.

This enable the usage of relative short-lived radiopharmaceuticals in in blood flow imaging for measurements using PET or SPECT.

In an embodiment the recipient is a device for intravenous (IV) administration of said liquid radioactive solution in said bolus conduit into a human or animal body.

In an embodiment the device for IV administration is an injection needle and/or a Peripheral venous catheter and/or an arterial catheter.

In an embodiment the method is a therapeutic method.

In a second aspect the invention relates to an infusion system for delivering a liquid radioactive solution from a source to a recipient, said system comprising:
  a radiation detector,
  a first valve having a waste position and a recipient position,
  a bolus conduit, a waste conduit and a recipient conduit, each conduit having a valve end being connected to said first valve, so that the first valve can establish a waste flow path in the waste position and a recipient flow path in the recipient position, the recipient flow path being different from said waste flow path,
  wherein the waste flow path is defined by the bolus conduit and the waste conduit, and the recipient flow path is defined by the bolus conduit and the recipient conduit,
  wherein the bolus conduit comprises a bolus inlet adapted to receive the radiopharmaceutical solution from the source, the waste conduit comprises a waste outlet adapted for flow out of said waste conduit and the recipient conduit comprises a recipient outlet adapted for flow out of said recipient conduit to a recipient,
  wherein the bolus conduit comprises a measuring section and a specific internal volume, the radiation detector being operable to determine a reference level of radioactivity of the solution present in said measuring section,
  wherein the waste flow path establishes liquid communication between said bolus inlet and said waste outlet, and the recipient flow path establishes liquid communication between the bolus inlet and the recipient outlet.

In an embodiment the measuring section extends from the bolus inlet towards the valve end.

In an embodiment the method relates to the transport of a radioactive solution for use in blood flow imaging using PET (Positron emission tomography) scanning technology or SPECT (photon emission computed tomography) scanning methodology.

In an embodiment the infusion system comprises:
  a second valve having an inlet position and a flushing position,
  a flushing conduit and a source conduit, each conduit having a valve end being connected to said second valve, the source conduit being adapted for transporting the radioactive solution from the source into the bolus conduit, when the second valve is in the inlet position,
  a flushing liquid reservoir comprising a flushing liquid, said flushing liquid reservoir being connected to said flushing conduit,
  a flushing device being adapted for transporting the flushing liquid from the flushing liquid reservoir through said flushing conduit and into the bolus conduit, when the second valve is in the flushing position.

In an embodiment the flushing liquid reservoir may be connected directly to said flushing conduit.

In an embodiment the flushing device may be connected to the flushing conduit.

In an alternative embodiment the flushing device is formed by the flushing reservoir and a pump. The pump and flushing reservoir being connected to the flushing conduit. The pump being adapted to pump liquid into or out of the flushing reservoir.

In the content of this specification the term "pump" may be viewed as any type of suitable pump.

In an embodiment the pump is a positive displacement pump.

A positive displacement pump makes a fluid move by trapping a fixed amount and forcing (displacing) that trapped volume into the discharge pipe.

In an embodiment the specific internal volume of the bolus conduit is approximately 0.1-50 ml, preferably approximately 1-10 ml and most preferred approximately 2 ml.

In an embodiment the measuring section is spiral-shaped or helically shaped or coil shaped.

In an embodiment the measuring section comprises at least 1 winding, preferably 1-50 windings, more preferred 5-25 windings.

The number of windings are selected in relation to the desired dosing volume and the inner diameter of the conduit In an embodiment a part of the radiation detector is arranged within the measuring section, so that said measuring section wreathes said part of the radiation detector.

In an embodiment a sterile filter is arranged between the source and the bolus conduit, so that the radioactive solution from the source flows trough said sterile filter before reaching the bolus conduit.

In an embodiment a second radiation detector and/or a bubble detector is arranged adjacent to the recipient conduit.

The second radiation detector and/or the bubble detector increases the security level of the infusion system.

The second radiation detector and/or the bubble detector may be connected to a computer means.

The radiation detector is adapted to detect a leakage upstream in the infusion system.

If after the transportation of the radioactive solution in the bolus conduit to the recipient is initiated, and the radiation detector measure a pre-selected warning level and/or alarm level. These levels may vary depending on the usage of the infusion system. The level may be approximately zero.

The levels may both be too low and/or too high in relation to an expected level of radiation.

The levels may be automatically selected or manually selected.

If the measured amount of radiation reaches the warning level, a warning sign may be signalled. The warning sign may be visual and/or audible or a combination thereof.

If the measured amount of radiation reached the alarm level, the transportation of liquid to the recipient may be interrupted.

In an embodiment the second radiation detector records the bolus injection profile and reports the profile to a user during injection, and the computer means records the injection profile in a batch report.

Furthermore, the second radiation detector may be coupled with the first radiation detector as an extra safety mechanism, so that in the event that the pump initiates injection, and the radioactivity does not leave the first radiation detector fast enough and/or does not arrive within an expected time frame at the third radiation detector, the computer means also stops the injection.

This feature of double coupled detectors with a time stamp estimate covers the risk of having a leakage between the syringe as well the connector to the recipient conduit.

The feature also covers the risk of the syringe sucking a vacuum, and upon initiation of injection will have insufficient volume to complete the injection as planned.

The bubble detector is adapted to detect the presence of air in the radioactive solution being transported from said bolus conduit to the recipient. If the bubble detector detects an amount of air equal to or higher than a preselected alarm level, the transport of the radioactive solution to the recipient may be interrupted.

In an embodiment the infusion system is a sterile infusion system.

In an embodiment the radioactive solution comprises a radiopharmaceutical having a radioactive half-life of less than 21 minutes, preferably less than 10 minutes, more preferred less 3 minutes.

In an embodiment the recipient conduit comprises a second sterile filter.

In an embodiment the waste conduit comprises a check valve and/or a pump.

The pump is adapted to transport accumulated liquid from the first sterile filter to the waste outlet. The pump functions solely in a forward motion, where the principal purpose of the pump is to facilitate a more rapid transport of the radioactive solution across the sterile filter and into the bolus conduit.

In some embodiments the pump is a positive displacement pump.

The recipient system may also comprise a check valve. The check-valve may be a single way check valve.

The check valve prevents a possible back flow from the recipient to the system, thereby preventing cross-contamination of for example viruses, that otherwise would not be caught with a sterile filter due to their size (less than 22 micrometers, which corresponds to a size of pores in a sterile filter).

In an embodiment said recipient is a device for intravenous (IV) administration of said liquid radioactive solution in said bolus conduit into a human or animal body.

In an embodiment the device for IV administration is an injection needle and/or a Peripheral venous catheter and/or an arterial catheter.

In an embodiment the infusion system according to the second aspect is computer controlled.

In an embodiment the computer controlled infusion system may also be manually controlled.

The infusion system may also comprise a computer means with a data storage unit. The data storage unit being operable to store data received from different elements of the infusion system.

The data may be; injection speed, pump speed profile, measuring section volume, bolus conduit volume, radiation profile measured by the secand radiation detector, radiation profile measured by the first radiation detector, measurements from the bubble detector etc.

The computer means may comprise a display, the display being adapted for visually displaying said data.

Even if the infusion system is computer controlled, a user may manually overwrite the settings.

Thereby a user is able to initiate or delay the transportation to the recipient depending on the situation.

In another embodiment of the first or second aspect, the liquid solution of a radiopharmaceutical is held in the bolus conduit for a relevant holding time until a desired radioactivity level is attained by natural radioactive decay, before being moved out of said bolus conduit.

In another aspect the invention relates to a use of an infusion system according to the second aspect in a method of delivering a liquid radioactive solution according to the first aspect.

In another embodiment the invention relates to a bolus of a radioactive solution obtainable by the method of delivering a liquid radioactive solution according to the first aspect.

In a third aspect the invention relates to a non-surgical method of dosing a liquid radioactive solution having a desired final level of radioactivity and a final volume comprising the steps of:
- determining said desired final level of radioactivity and final volume of the radioactive solution to be produced,
- providing a first valve having a waste position and a dosing position,
- providing a bolus conduit 30, a waste conduit 40 and a dosing conduit 50, each conduit having a valve end being connected to said first valve, so that the first valve can establish a waste flow path in the waste position and a dosing flow path in the dosing position, the dosing flow path being different from said waste flow path, the bolus conduit comprising a measuring section and an internal volume, the internal volume being approximately equal to the desired final volume of the radioactive solution,
- arranging said first valve in the waste position,
- transporting a first amount of said radioactive solution through said waste flow path, the first amount of said radioactive solution having an initial level of radioactivity that is at least approximately equal to or higher than the desired final level of radioactivity and an initial volume that is larger than the internal volume of said bolus conduit,
- providing a radiation detector, the radiation detector being operable to measure a level of radioactivity of the radioactive solution in said measuring section,
- measuring a reference level of radioactivity of said radioactive solution present in said measuring section,
- wherein that when the reference level of radioactivity is approximately equal to a pre-final level of radioactivity, the method further comprises the steps of:
- arranging the first valve in the dosing position, and
- transporting the radioactive solution present in the bolus conduit through the dosing flow path, so that the radioactive solution has the desired final level of radioactivity when said radioactive solution reaches the end of the dosing flow path.

The administered dose (D) dose of a radiopharmaceutical having a radioactive half-life of <21 minutes should be of a size suitable to the detection limit of the scanner, local scanner settings and conditions as well as the individual patients age, weight, sex and ethnicity.

The bolus volume (V) should be of a size to allow for a subsequently rapid introduction into the body, and suitable as regards the individual patients age, weight, sex and ethnicity. For different diagnostic purposes (V) will be within the range of 0.05-50 ml.

The injection speed (S) should be sufficiently fast to allow for a subsequently rapid introduction of the volume (V) into the body, and suitable as regards the individual patients age, weight, sex and ethnicity. The skilled person will understand, that in the scope of the present invention the methods described in relation to the first and third aspects may in some embodiments not fall within the range of methods for treatment of the human or animal body by surgery or therapy and diagnostic methods practised on the human or animal body, since the methods according to the invention in some embodiments are of a technical character and are in these embodiments not carried out on the living human or animal body, as the term "recipient" may in the scope of the invention be a device/means for receiving the radioactive solution.

A person skilled in the art will appreciate that any and all of the above embodiments, options and developments may be combined with each other in accordance with the present invention.

THE DRAWINGS

In the enclosed schematic drawings, which show non-binding examples of embodiments of the present invention.

DESCRIPTION OF DETAILED EMBODIMENTS OF THE INVENTION

Figure 1:
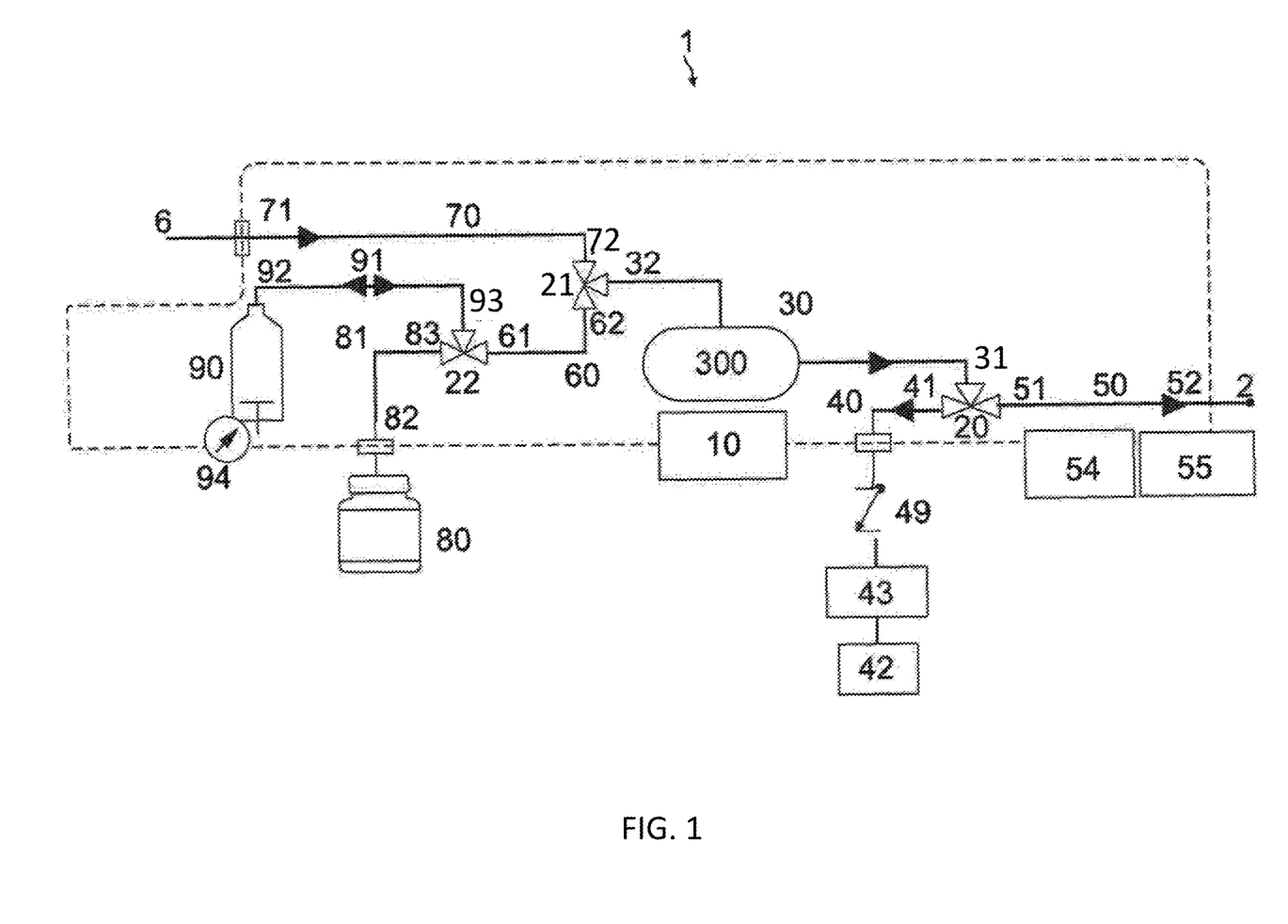
FIG. 1 shows a schematic overview of the infusion system according to the invention.

FIG. 1 shows a first embodiment of an infusion system 1 according to the present invention, the infusion system being suitable for delivering a liquid radioactive solution to a recipient 2.

The radioactive solution is transported from a source 6 to the recipient 2 according to an embodiment of the method according to the invention comprising the steps of:

The infusion system 1 comprises; a first valve 20 having a waste position and a recipient position, a radiation detector 10, a bolus conduit 30, a waste conduit 40 and a recipient conduit 50, each conduit 30, 40, 50 having a valve end 31, 41, 51 being connected to said first valve 20.

The first valve 20 establishes a waste flow path in the waste position, wherein the waste flow path is defined by the bolus conduit 30 and the waste conduit 40.

The first valve 20 establishes a recipient flow path in the recipient position, wherein the recipient flow path is defined by the bolus conduit 30 and the recipient conduit 50.

The recipient flow path is different from said waste flow path.

The bolus conduit 30 comprises a bolus inlet 32 adapted to receive the radiopharmaceutical solution from the source 6.

The bolus conduit 30 comprises a specific internal volume.

The bolus inlet 32 is opposite of the valve inlet end 31.

Liquid flow through in the bolus conduit 30 is preferably from the bolus inlet 32 towards the valve end 31.

Flow through the bolus conduit 30 may be either the radioactive solution and/or a flushing liquid.

The first valve 20 is preferably a three-way valve.

The waste conduit 40 comprises a waste outlet 42 adapted for flow out of said waste conduit 40.

Flow through the waste conduit 40 may be either the radioactive solution and/or the flushing liquid.

The recipient conduit 50 comprises a recipient outlet 52 adapted for flow out of said recipient conduit 50 to a recipient 2.

Flow through the recipient conduit 50 may be either the radioactive solution and/or the flushing liquid.

The recipient outlet 52 is in fluid communication with the recipient 2.

The bolus conduit 30 comprises a measuring section 300. The radiation detector 10 is arranged in relation to the measuring section 300, so that the radiation detector 10 is able to determine a reference level of radioactivity of the solution present in said measuring section 300.

Figure 2:
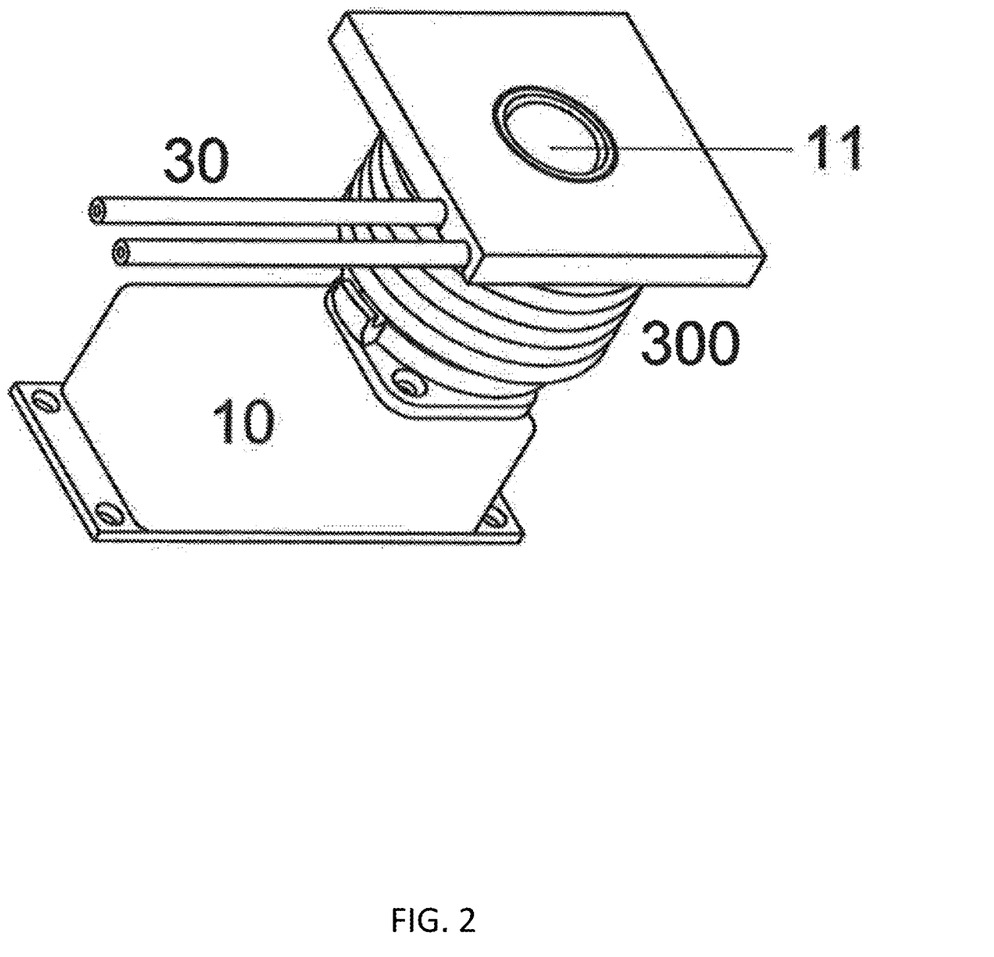
FIG. 2 shows a part of an embodiment of the infusion system.

An embodiment of the measuring section 300 is shown in FIG. 2.

The waste flow path establishes liquid communication between said bolus inlet 32 and said waste outlet 42. The recipient flow path establishes liquid communication between the bolus inlet 32 and the recipient outlet 52.

The infusion system 1 further comprises a second valve 21. The second valve having an inlet position, a flushing position and a suction position.

The infusion system 1 further comprises a flushing conduit 60 and a source conduit 70.

The flushing conduit 60 comprises a valve end 62 and an opposite flushing source end 61. The source conduit 70 comprises a valve end 72. Each valve end 62, 72 is connected to said second valve 21.

The bolus inlet 32 of the bolus conduit 30 is also connected to said second valve.

The source conduit 70 is adapted for transporting the radioactive solution from the source 6 to the bolus conduit 30, when the second valve 21 is in the inlet position.

The infusion system 1 further comprises a flushing liquid reservoir 80 comprising a flushing liquid.

The flushing liquid is preferably a saline solution.

The flushing liquid may also be a buffered saline solution such as phosphate buffered saline.

In an embodiment the solution is approximately of near osmolality with the recipient's plasma, and preferably approximately osmolar with the recipient's plasma or considered to be approximately iso-osmolar.

In an embodiment the flushing liquid reservoir 80 may be connected to the flushing source valve end 61 of the flushing conduit 60.

The infusion system 1 further comprises a third valve 22, the third valve having a first, second and third position. The third valve is connected to the flushing source end 61 of the flushing conduit 60.

In an embodiment the third valve may be a three-way valve.

The flushing liquid reservoir 80 further comprises a flushing reservoir conduit 81. The flushing reservoir conduit 81 having one end 83 connected to the third valve 22 and another, opposite end 82 connected to the flushing liquid reservoir 80.

The flushing reservoir conduit 81 allows liquid flow between the flushing liquid reservoir 80 and the third valve 22.

A connector may be arranged between the flushing liquid reservoir 80 and the flushing reservoir conduit 81.

The infusion system 1 further comprises a flushing device 90. The flushing device 90 may be a syringe. The syringe may be automatic and/or manually controlled.

The flushing device 90 comprises a flushing device conduit 91 having one end 92 connected to said flushing device 90 and another, opposite end 93 connected to the third valve 22.

The flushing device 90 is adapted for transporting liquid into itself and/or liquid from within itself and out of itself.

The third valve 33 being in the first position establishes fluid communication between the flushing device 90 and the flushing liquid reservoir 80. In this position the flushing device 90 is able to transport flushing liquid from the flushing liquid reservoir 80 and into itself 90 through the flushing reservoir conduit 81, the third valve 22 and the flushing device conduit 91.

The transport may also be from the flushing device 90 to the flushing liquid reservoir 80.

The third valve 33 being in the second position establishes fluid communication between the flushing device 90 and the flushing conduit 60. Depending on the position of the second valve 21, fluid communication is also established between the flushing device 90 and the source conduit 70 and thereby the source 6, and/or the flushing device 90 and the waste flow path, and/or the flushing device 90 and the recipient flow path.

The third valve 22 being in the first position, allows the flushing device 90 to transport an amount of the flushing liquid from the flushing reservoir 80 to itself 90.

Subsequently arranging the third valve 22 in the second position and arranging the second valve 21 in the flushing position enables the flushing device 90 to transport an amount of the flushing liquid contained in itself 90 into the bolus conduit 30.

The second valve 21 being in the suction position establishes fluid communication between the source conduit 70 and the flushing conduit 60. If the third valve 22 is simultaneously in its second position, fluid communication is established between the flushing device 90 and the source 6.

This allows the flushing device 90 to transport an amount of the radioactive solution present from the source and into itself 90.

Subsequently arranging the third valve 22 in the first position, allows the flushing device 90 to transport an amount of the flushing liquid from the flushing reservoir 80 to itself 90.

Thereby the radioactive solution may be mixed with an amount of flushing liquid.

Alternatively, or additionally, the third valve 22 is arranged in the second position and the second valve 21 is arranged in the flushing position, this enables the flushing device 90 to transport an amount of the content of itself 90 into the bolus conduit 30.

The flushing device 90 is adapted to transport liquids at a pre-selected speed. The speed setting may vary depending on usage of the infusion system.

The speed may also vary during a single transportation, so that the transported liquid entering the recipient has a specific injection profile. The injection profile may be measured with a radiation detector.

The flushing device 90 is adapted to contain a volume of liquid, said volume of liquid being at least approximately equal to or larger than the total internal volume of the conduits that defined a flow path from the flushing device 90 to the recipient 2.

In the specific embodiment shown on FIG. 1, the conduits that define the flow path from the flushing device 90 to the recipient 2 are; the flushing device conduit 91, the flushing conduit 60, the bolus conduit 30 and the recipient conduit 50.

The volume of liquid that the flushing device is adapted to contain is preferably up to 250 ml, but more preferably up to 100 ml, and most preferably up to 60 ml.

It is to be understood that the volume of liquid the flushing device is adapted to contain shall as a minimum be of a size allowing for flushing of the entire flow path from the flushing device into the recipient.

The flushing device 90 comprises a force sensor 94. The force sensor 94 being adapted to continuously measure the amount of force used to transport the liquid.

The force sensor 94 may have a pre-selected warning level and/or alarm level. These levels may vary depending on the usage of the infusion system.

The levels may both be too low and/or too high in relation to the preselected speed of the transportation.

The levels may be automatically selected or manually selected.

If the measured amount of force used reaches the warning level, a warning sign may be signalled. The warning sign may be visual and/or audible or a combination thereof.

If the measured amount of force used reached the alarm level, the transportation of liquid to the recipient may be interrupted.

The specific internal volume of the bolus conduit 30 is approximately 0.1-50 ml, preferably approximately 1-10 ml and most preferred approximately 2 ml.

The infusion system 1 further comprises a second radiation detector 54 and/or a bubble detector 55.

The second radiation detector 54 is arranged in relation to the recipient conduit 50, so that the radiation detector 54 is able to determine a level of radioactivity of the solution being transported from said bolus conduit 30 said recipient 2.

The waste conduit 40 comprises a check valve 49. The check valve is a single way check valve.

The waste conduit 40 comprises a decay conduit 43.

The length of the decay conduit 43 may be dependent on the amount of liquid that is transported to the waste. This is again for example dependent on the amount of radioactive solution transported into the infusion system from the source.

The waste conduit may be connected to an external collection vessel of a suitable size.

The infusion system of FIG. 1 may be used in a method according to the first aspect of the invention.

FIG. 1 also shows an embodiment of the infusion system according to the present invention, the infusion system 1 being suitable for delivering a liquid radioactive solution from a source 6 to a recipient 2.

Before commencing the delivery of the liquid radioactive solution from the source 6 to the recipient 2, a suitable infusion system 1 is selected, the infusion system depending on the type of delivery to be done.

A new recipient system 200 is selected to ensure, that no cross contamination occurs between recipients.

Before connecting the infusion system 1 to the recipient 2, if any liquid is present in the infusion system a recovery mode setting is initiated, wherein the infusion system is flushed with flushing liquid. The flushing liquid flowing out of the system through the waste outlet 42 and/or the recipient system outlet 252.

In an embodiment the flushing of the system is done by arranging the second valve 21 in the flushing position, arranging the third valve 22 in the third position and transporting the flushing liquid from the flushing reservoir 80 through the flushing conduit 60, through the bolus conduit 30 and depending on the position of the first valve 20, which position may change during the flushing, through the waste conduit 40 and/or the recipient conduit 50 and the reciplent system 200.

To initiate the delivery of the radioactive solution from the source 6 to the recipient 2, the following steps are performed:

The third valve 22 is arranged the first position.

The flushing device 90 transports an amount of flushing liquid from the flushing liquid reservoir 80 and into itself via the flushing reservoir conduit 81, the third valve 22 and the flushing device conduit 91.

The third valve 22 is then arranged in the second position.

A desired recipient level of radioactivity and recipient volume of the radioactive solution to be delivered to the recipient is determined.

The first valve 20 is arranged in the waste position.

The second valve 21 is arranged in the inlet position.

A first amount of said radioactive solution is transported through said source conduit 70 and the waste flow path.

The first amount of said radioactive solution has an initial level of radioactivity that is at least approximately equal to or higher than the desired recipient level of radioactivity and an initial volume that is larger than the internal volume of said bolus conduit.

The first radiation detector 10 measures a reference level of radioactivity of the radioactive solution in said measuring section.

When the reference level of radioactivity is approximately equal to an injection level of radioactivity, the first valve 20 is then arranged in the recipient position, the second valve 21 is arranged in the flushing position The flushing liquid is then transported through the flushing device conduit 91, the third valve 22, the flushing conduit 60, the second valve 21, the bolus conduit 30, the first valve 20, the recipient conduit 50 and the recipient system 200, whereby the liquid radioactive solution in the bolus conduit 30 is transported through the recipient flow path and to the recipient.

FIG. 2 shows an embodiment of the measuring section 300 and the radiation detector 10.

The measuring section 300 is coil shaped.

A part 11 of the radiation detector 10 is arranged within the measuring section 300.

Said measuring section 300 wreathes said part 11 of the radiation detector.

In an embodiment the total bolus conduit 30 volume is approximately 2 ml, the total length of the bolus conduit is 1.85 m and the conduit has an inner diameter of 1.25 mm.

In an embodiment the total inner volume of the measuring section 300 is approximately equal to the total inner volume of the bolus conduit 30.

Figure 3:
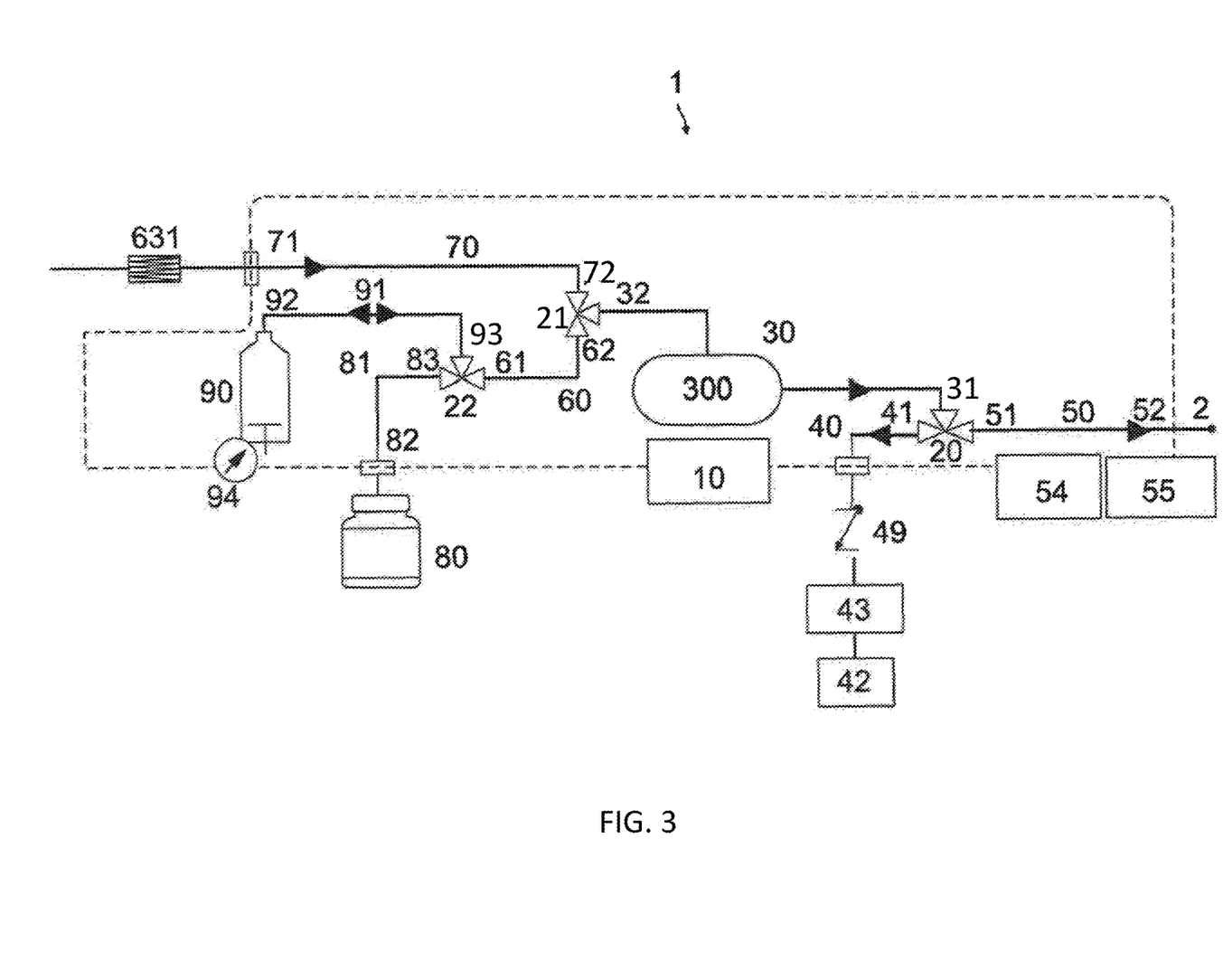
FIG. 3 shows a schematic overview of an embodiment of the infusion system according to the invention

FIG. 3 shows an embodiment of the infusion system 1 according to the invention.

A first sterile filter 60 is arranged between the source 6 and the bolus conduit 70. This sterile filter 60 is arranged so that the radioactive solution from the source 6 flows trough said sterile filter 60 before reaching the source conduit and/or the bolus conduit 60.

The infusion system 1 is a sterile infusion system.

The infusion system 1 further comprises a recipient system 200. The recipient system 200 is arranged between the recipient conduit 50 and the recipient 2. The recipient system establishes fluid communication between the recipient conduit 50 and the recipient 2.

The recipient system 200 may form part of the recipient flow path.

The recipient system 200 comprises recipient system conduit 250. The conduit 250 comprising a recipient system outlet 252 adapted for flow out of said recipient system conduit 250 to the recipient 2.

The recipient system conduit 250 also comprises an infusion system end 251 opposite the recipient system outlet 252. The infusion system end 251 being connected to the recipient outlet 52 of the recipient conduit 50.

The recipient system 200 further comprises a sterile filter 260 arranged between the infusion system end 251 and the recipient system outlet 252, so that liquid transported in said recipient system conduit 250 from the infusion system end 251 towards the recipient system outlet 252 passes the sterile filter 260 before reaching the recipient.

The recipient system 200 also comprise a check valve 209. The check-valve is a single way check valve.

The check valve prevents a possible back flow from the recipient to the system, thereby preventing cross-contamination of for example viruses.

The check valve 209 is arranged downstream of the sterile filter 260, between the sterile filer 260 and the recipient system outlet 252.

The recipient 2 is a device for intravenous (IV) administration of said liquid radioactive solution in said bolus conduit 30 into a human or animal body. The device for IV administration may be an injection needle and/or a Peripheral venous catheter and/or an arterial catheter.

Figure 4:
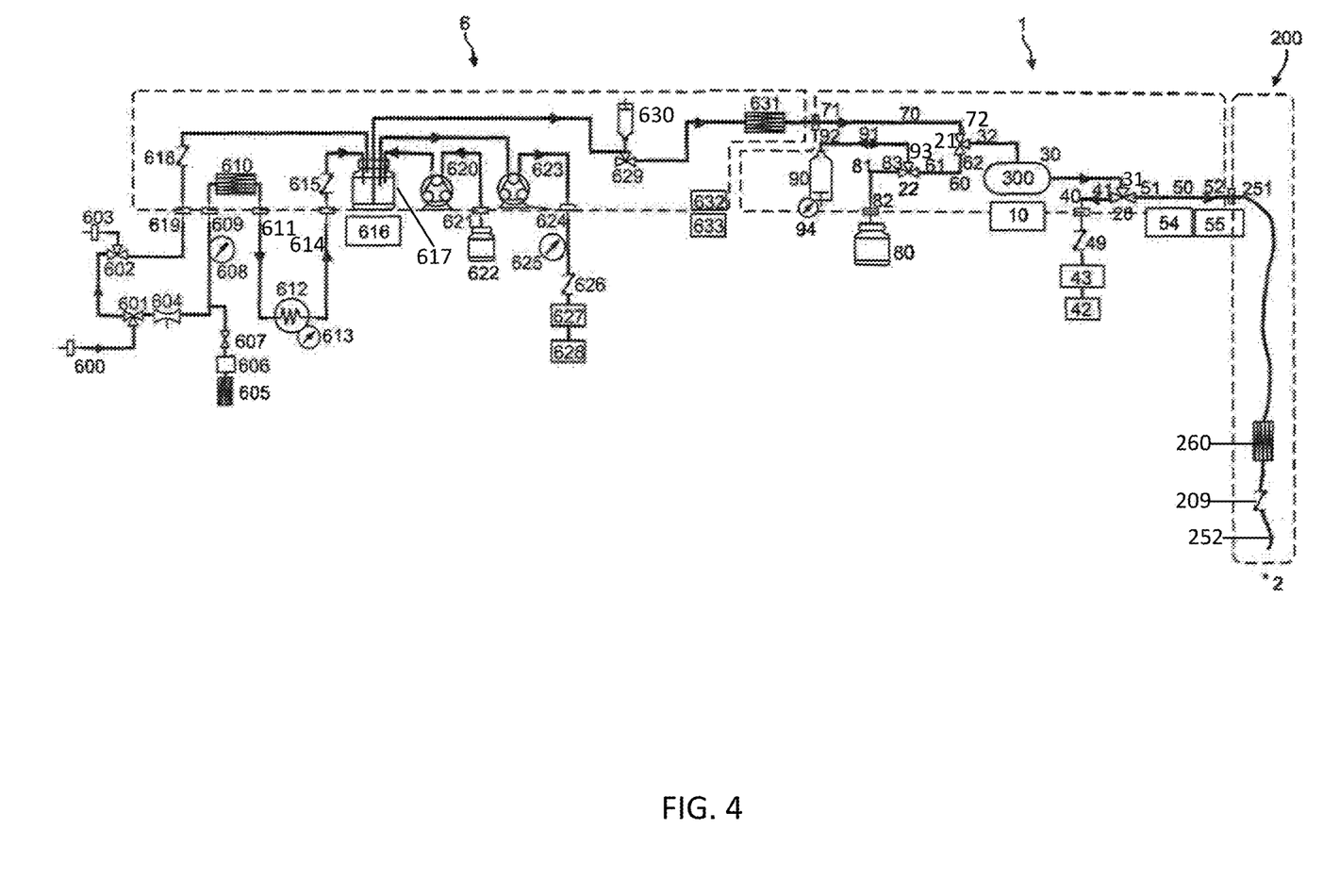
FIG. 4 shows a schematic overview of another embodiment of the infusion system, wherein the infusion system is connected to a production system 6 and a recipient system 200.

FIG. 4 shows a schematic overview of another embodiment of the infusion system, wherein the infusion system is connected to a production system 6 and a recipient system 200.

In an embodiment the infusion system and/or the production system 6 and/or the recipient system 200 is exchangeable.

Thereby a fixed hardwired system (elements outside the dashed lines) is present in the overall system and the different system parts 6, 1, 200 may be changed as desired.

This providing an easy and cost effective way of switching between different measurements with different requirement, whilst still ensuring no cross contamination between patients and that the entire system is sterile.

The production system 6 comprises everything inside the appertaining dashed line. The production system 6 and the hardwired system are connected by a number of connections, namely connection 609, 611, 614, 619, 621 and 624.

The production system 6 may be exchanged daily.

When a new production system 6 is connected to the hardwired system, a RFID System ID reader 633 may read the information on the production systems' RFID System ID tag 632 to ensure that the system has not been used previously.

In an embodiment the infusion system 1 also comprises a RFID System ID tag and/or the hardwire system comprises an appertaining RFID System ID reader for ensuring that the infusion system has not been used before.

The process of producing the radioactive solution, here exemplified with O-15 H2O, will be described in the following and in relation to FIG. 4.

Radioactive O-15 O2 gas is delivered from a cyclotron (not shown) and mixed with hydrogen. Nitrogen is used as carrier-gas. This gas will in the following be mentioned as 'O-15 H2O gas'.

The gas enters the production system 6 though an inlet connection 600 and is transported to a valve 601 and/or another valve 602.

The positions of valve 601 and valve 602 are controlled simultaneously, so that they always change position in parallel, thereby they control which way the gas passes through the system. The radioactive gas is either passed directly from valve 601 to valve 602 (on FIG. 4 the gas is transported to the left side after valve 601) and then towards outlet connection 603, or the gas is transported into the system (in which case the gas goes right after valve 601 on FIG. 4) before being looped back around through other elements (such as 612, 616, 618, 619) and then exiting at connection 603.

When the delivery of gas begins, the gas is to be sent directly out of the system. Therefore, valve 601 is in the position that directs the radioactive O-15 O2 gas directly towards valve 602, which in turn is in the position that directs the radioactive gas towards outlet connection 603.

The construction of valve 602 does not allow the radioactive O-15 O2 to pass from valve 602 towards connection 619.

A check valve 618 is present ensure that no backflow of gas towards a mixer 617 is possible.

The mixer 617 has five tubes connected to it, all entering at the top and ending inside the mixer at differing levels, their openings facing the bottom of the mixer 617.

When the delivery of O-15 O2 gas begins, the fill up of saline from a saline reservoir 622 into the mixer 617 also begins.

A pump 620 starts running to pump saline from the saline reservoir 622 through a tube extends into the mixer 617 and ends close to the top of said mixer 617.

Pump 623 also starts running. This pump 623 pumps air and/or excessive water out from the mixer 617 through another tube. This tube is located inside the mixer at a distance from the bottom of said mixer 617, thereby defining the maximum volume of saline that can be filled into the mixer 617.

To avoid a negative pressure (i.e. an under pressure) in the system whilst pump 623 is pumping out air, valve 607 is set to an on-position to let air pass into the system through compressor 606 and sterile filter 605.

When the compressor 606 is not on, it comprises a function that allows air to pass from its inlet (below 606 on FIG. 4) to its outlet (above 606 on FIG. 4) when there is an under pressure on its outlet side.

When the mixer 617 is filled it will maintain a volume that is below or approximately equal to the volume defined by the tube that transports saline in from the saline reservoir 622. This may be dependent on a pre-set value or by the user requested production saline volume.

Then pump 620 stops running after which pump 623 stops running. Valve 607 is set to an off-position to stop the allowance of air to enter the system through sterile filter 605 and compressor 606, as this is no longer needed when pump 623 is not running.

The positions of valve 601 and valve 602 are now changed in parallel, to allow the O-15 O2 gas to pass through the mixer 617.

On its way to the mixer 617 the gas passes through;
a flow sensor 604, to ensure that the flow rate of the gas is within a defined allowed range,
a pressure sensor 608, which is connected at a T-piece, to ensure that the pressure of the gas is within a defined allowed range,
a connection 609,
a sterile filter 610 to ensure that the gas is sterile,
another connection 611 and therefrom
into an oven 612 in which it is heated up to create O-15 H2O gas.

The temperature of the oven 612 is monitored by temperature sensor 613.

The O-15 H2O gas is then passed through another connection 614 and another check valve 615 before finally entering the mixer 617 through a tube, that extends into the mixer and has an ending arranged relatively close to the bottom of the mixer 617 (not visible from the drawing).

Thereby the O-15 H2O gas bubbles through the saline present in the mixer 617, in which a very large percentage of the radioactive O-15 H2O is dissolved, before exiting the mixer 617 through a tube, said tube having an opening arranged relatively close to the top of the mixer 617.

The gas, which now consists mostly of a nitrogen carrier gas, is passed through a check valve 618 and a connection 619, through valve 602 which directs it towards connection 603, where it exits the production system.

The bubbling of gas in the mixer 617 continues until the requested production level in mixer 617 is detected by radioactivity sensor 616.

Then valve 601 and 602 again change position in parallel. Valve 601 is set to the position that directs the radioactive O-15 O2 gas directly towards valve 602, which is set to the position that directs the radioactive gas towards outlet connection 603.

The radioactive O-15 H2O in the mixer 617 is then drawn up into syringe 630 whilst valve 629 is set to a position that allows this.

The tube inside the mixer 617 through which the O-15 H2O is drawn up has its opening arranged approximately at the bottom of the mixer, ensuring that all the O-15 H2O will be drawn up.

As the volume of syringe 630 is larger than the maximum volume of the O-15 H2O in mixer 617, air is also drawn up into syringe 630.

Then the position of valve 629 is changed to allow passage of the content of the syringe towards a sterile filter 631.

The content of syringe 630 is thus emptied towards the sterile filter 31, through which the O-15 H2O passes first, followed by the air, which is let out of sterile filter 631, as it is a vented filter.

Thereby the production of the O-15 H2O is complete.

The amount of O-15 H2O that thereafter enters the infusion system, is referred to as the first amount of the radioactive solution.

The transportation of O-15 H2O from the production system 6 (i.e. the source) to the recipient 2 is explained in relation to FIGS. 1-3.

The skilled person will understand that the term "dosing position" corresponds to the "recipient position", the "dosing conduit" corresponds to the "recipient conduit", the "dosing outlet" corresponds to the "recipient, the "dosing flow path" corresponds to the "recipient flow path", the "final level" corresponds to the "recipient level", and that the terms are used in relation to the same elements but in different claims to avoid confusion.

The invention claimed is:

1. A non-surgical method of delivering a liquid radioactive solution from a source to a recipient comprising the steps of:
    determining a desired recipient level of radioactivity and recipient volume of the radioactive solution to be delivered to the recipient,
    providing a first valve having a waste position and a recipient position,
    providing a bolus conduit, a waste conduit and a recipient conduit, each conduit having a valve end being connected to said first valve, so that the first valve can establish a waste flow path in the waste position and a recipient flow path in the recipient position, the recipient flow path being different from said waste flow path, the bolus conduit comprising a measuring section and an internal volume, the internal volume being approximately equal to the desired recipient volume of the radioactive solution to be delivered to the recipient,
    arranging said first valve in the waste position,
    transporting a first amount of said radioactive solution through said waste flow path, the first amount of said radioactive solution having an initial level of radioactivity that is at least approximately equal to or higher than the desired recipient level of radioactivity and an initial volume that is larger than the internal volume of said bolus conduit,
    providing a radiation detector, the radiation detector being operable to measure a level of radioactivity of the radioactive solution in said measuring section,
    measuring a reference level of radioactivity of said radioactive solution present in said measuring section,
    characterized in that when the reference level of radioactivity is approximately equal to an injection level of radioactivity, the method further comprises the steps of:
    arranging the first valve in the recipient position,
    transporting the radioactive solution present in the bolus conduit through the recipient flow path,
    providing a second valve having an inlet position and a flushing position,
    providing a flushing conduit and a source conduit, each conduit having a valve end being connected to said second valve, the source conduit being adapted for transporting the first amount of said radioactive solution from the source into the bolus conduit, when the second valve is in the inlet position,
    providing a flushing liquid reservoir comprising a flushing liquid, said flushing liquid reservoir being connected to said flushing conduit, and
    providing a flushing device being adapted for transporting the flushing liquid from the flushing liquid reservoir through said flushing conduit and into the bolus conduit, when the second valve is in the flushing position.

2. A non-surgical method of delivering a liquid radioactive solution according to claim 1, wherein the injection level of radioactivity of the radioactive solution differs at most ±10% from the desired recipient level of radioactivity.

3. A non-surgical method of delivering a liquid radioactive solution according to claim 1, further comprising:
    before the step of transporting a first amount of said radioactive solution through said waste flow path, arranging the second valve in the flushing position, and transporting the flushing liquid through the flushing conduit and through the bolus conduit.

4. A non-surgical method of delivering a liquid radioactive solution according to claim 1, wherein the step of transporting the radioactive solution present in the bolus conduit through the recipient flow path comprises:
    arranging the second valve in the flushing position, and transporting the flushing liquid through the flushing conduit, through the bolus conduit and the recipient conduit, whereby the liquid radioactive solution in the bolus conduit is moved through the recipient flow path and to the recipient.

5. A non-surgical method of delivering a liquid radioactive solution according to claim 1, wherein a second radiation detector and/or a bubble detector is arranged adjacent to the recipient conduit.

6. A non-surgical method of delivering a liquid radioactive solution according to claim 1, wherein the specific internal volume of the bolus conduit is approximately 0.1-50 ml.

7. A non-surgical method of delivering a liquid radioactive solution according to claim 1, wherein the radioactive solution comprises a radiopharmaceutical having a radioactive half-life of less than 21 minutes.

8. A non-surgical method of delivering a liquid radioactive solution according to claim 1, wherein said recipient is a device for intravenous (IV) administration of said liquid radioactive solution in said bolus conduit into a human or animal body.

9. A non-surgical method of delivering a liquid radioactive solution according to claim 1, wherein
an injection speed of the radioactive solution to the recipient is approximately 0.05-7 ml/second, and/or
the liquid radioactive solution in the bolus conduit is moved out of said bolus conduit in less than approximately 5 seconds, and/or
the liquid radioactive solution is transported out of said recipient conduit and to said recipient in less than approximately 10 seconds.

10. A non-surgical method of delivering a liquid radioactive solution according to claim 1, wherein the measuring section is spiral-shaped or helically shaped or coil shaped.

11. A non-surgical method of delivering a liquid radioactive solution according to claim 10, wherein a part of the radiation detector is arranged within the measuring section, so that said measuring section wreathes said part of the radiation detector, the radiation detector being operable to determine a level of radioactivity of the solution in the measuring section.

12. A non-surgical method of dosing a liquid radioactive solution having a desired final level of radioactivity and a final volume comprising the steps of:
determining said desired final level of radioactivity and final volume of the radioactive solution to be produced,
providing a first valve having a waste position and a dosing position,
providing a bolus conduit, a waste conduit and a dosing conduit, each conduit having a valve end being connected to said first valve, so that the first valve can establish a waste flow path in the waste position and a dosing flow path in the dosing position, the dosing flow path being different from said waste flow path, the bolus conduit comprising a measuring section and an internal volume, the internal volume being approximately equal to the desired final volume of the radioactive solution,
arranging said first valve in the waste position,
transporting a first amount of said radioactive solution through said waste flow path, the first amount of said radioactive solution having an initial level of radioactivity that is at least approximately equal to or higher than the desired final level of radioactivity and an initial volume that is larger than the internal volume of said bolus conduit,
providing a radiation detector, the radiation detector being operable to measure a level of radioactivity of the radioactive solution in said measuring section,
measuring a reference level of radioactivity of said radioactive solution present in said measuring section, characterized in that when the reference level of radioactivity is approximately equal to a pre-final level of radioactivity, the method further comprises the steps of:
arranging the first valve in the dosing position, and
transporting the radioactive solution present in the bolus conduit through the dosing flow path, so that the radioactive solution has the desired final level of radioactivity when said radioactive solution reaches the end of the dosing flow path,
providing a second valve having an inlet position and a flushing position,
providing a flushing conduit and a source conduit, each conduit having a valve end being connected to said second valve, the source conduit being adapted for transporting the first amount of said radioactive solution from the source into the bolus conduit, when the second valve is in the inlet position,
providing a flushing liquid reservoir comprising a flushing liquid, said flushing liquid reservoir being connected to said flushing conduit, and
providing a flushing device being adapted for transporting the flushing liquid from the flushing liquid reservoir through said flushing conduit and into the bolus conduit, when the second valve is in the flushing position.

13. A non-surgical method of dosing a liquid radioactive solution according to claim 12, wherein the pre-final level of radioactivity of the radioactive solution differs at most ±10% from the desired final level of radioactivity.

\* \* \* \* \*